United States Patent
Schatzberger

Patent Number: 6,142,991
Date of Patent: Nov. 7, 2000

[54] HIGH RESOLUTION CRYOSURGICAL METHOD AND APPARATUS

[75] Inventor: Shaike Schatzberger, Haifa, Israel

[73] Assignee: Galil Medical, Ltd., Yokneam, Israel

[21] Appl. No.: 09/052,165

[22] Filed: Mar. 31, 1998

[51] Int. Cl.$^7$ .................................................. A61B 18/18
[52] U.S. Cl. .............................. 606/21; 606/20; 606/23; 128/898
[58] Field of Search .................. 606/20–26; 128/898

[56] References Cited

U.S. PATENT DOCUMENTS

| | | | |
|---|---|---|---|
| 3,298,371 | 1/1967 | Lee | 606/23 |
| 5,190,539 | 3/1993 | Fletcher et al. | 606/25 |
| 5,433,717 | 7/1995 | Rubinsky et al. | 606/20 |
| 5,647,868 | 7/1997 | Chinn | 606/21 |
| 5,674,218 | 10/1997 | Rubinsky et al. | 606/20 |
| 5,741,248 | 4/1998 | Stern et al. | 606/21 |
| 5,833,685 | 11/1998 | Tortal et al. | 606/23 |

Primary Examiner—Michael Peffley

[57] ABSTRACT

A high resolution cryosurgical method and device for treating a patient's prostate are provided. The method includes the steps of (a) introducing a plurality of cryosurgical probes to the prostate, the probes having a substantially small diameter, the probes being distributed across the prostate, so as to form an outer arrangement of probes adjacent the periphery of the prostate and an inner arrangement of probes adjacent the prostatic urethra; (b) producing an ice-ball at the end of each of said cryosurgical probes, so as to locally freeze a tissue segment of the prostate. The apparatus includes (a) a plurality of cryosurgical probes of small diameter, the probes being for insertion into the patient's organ, the probes being for producing ice-balls for locally freezing selected portions of the organ; (b) a guiding element including a net of apertures for inserting the cryosurgical probes therethrough; and (c) an imaging device for providing a set of images, the images being for providing information on specific planes located at specific depths within the organ, each of said images including a net of marks being correlated to the net of apertures of the guiding element, wherein the marks represent the locations of ice-balls which may be formed by the cryosurgical probes when introduced through said apertures of the guiding element to said distinct depths within the organ.

13 Claims, 10 Drawing Sheets

HIGH RESOLUTION CRYOSURGICAL METHOD AND APPARATUS

FIELD AND BACKGROUND OF THE INVENTION

The present invention relates to high resolution cryosurgical method and apparatus which enable to effectively and accurately freeze and thereby destroy a predetermined portion of a tissue while minimizing damage to adjacent tissues and organs.

Cryosurgical procedures involve deep tissue freezing which results in tissue destruction due to rupture of cells and or cell organelles within the tissue. Deep tissue freezing is effected by insertion of a tip of a cryosurgical device into the tissue, either endoscopically or laparoscopically, and a formation of, what is known in the art as, an ice-ball around the tip.

In order to effectively destroy a tissue by such an ice-ball, the diameter of the ball should be substantially larger than the region of the tissue to be treated, which constraint derives from the specific profile of temperature distribution across the ice-ball.

Specifically, the temperature required for effectively destroying a tissue is about −40° C. or cooler. However, the temperature at the surface of the ice-ball is 0° C. The temperature declines exponentially towards the center of the ball such that an isothermal surface of about −40° C. is typically located within the ice-ball substantially at the half way between the center of the ball and its surface.

Thus, in order to effectively destroy a tissue there is a need to locate the isothermal surface of −40° C. at the periphery of the treated tissue, thereby exposing adjacent, usually healthy, tissues to the external portions of the ice-ball. The application of temperatures of between about −40° C. and 0° C. to such healthy tissues usually causes substantial damage thereto, which damage may result in temporary or permanent impairment of functional organs.

In addition, should the adjacent tissues are present at opposite borders with respect to the freeze treated tissue, such as in the case of prostate freeze treatments, as further detailed below, and since the growth of the ice-ball is in substantially similar rate in all directions toward its periphery, if the tip of the cryosurgical device is not precisely centered, the ice-ball reaches one of the borders before it reaches the other border, and decision making of whether to continue the process of freezing, risking a damage to close healthy tissues, or to halt the process of freezing, risking a non-complete destruction of the treated tissue, must be made.

Although the present invention is applicable to any cryosurgical treatment, discussion is hereinafter focused on a cryosurgical treatment of a patient's prostate.

Thus, when treating a tumor located at a patient's prostate, there is a trade-of between two options: (a) effectively destroying the prostatic tissue extending between the prostatic urethra and the periphery of the prostate and causing unavoidable damage to the patient's urethra or organs adjacent the prostate such as the rectum and nerves; (b) avoiding the damaging of the prostatic urethra and adjacent organs, but exposing the patient to the risk of malignancy due to ineffective destruction of the prostate tumor.

Currently, cryosurgery procedures for treating the prostate include the introduction of 5–7 probes into the prostate, the probes being typically arranged around the prostatic urethra such that a single probe is located, preferably centered, between the prostatic urethra and the periphery of the prostate. The dimensions of such a single probe are usually adapted for effectively treating the prostatic tissue segment extending from the urethra to the periphery of the prostate, e.g., a tip of 3 millimeters in diameter, generating an ice-ball of 3–4 centimeters in diameter, depending on the size of the prostate. Since a single ice-ball is used for freezing such a prostatic tissue segment, the volume of adjacent tissues exposed to damage is substantially greater than the volume of the treated tissue. For example, if the area of the ice-ball in cross section is $\pi R^2$, and an effective treatment of at least −40° C. is provided to an area of $\pi(R/2)^2$ (in cross section), then the area of adjacent tissues (in cross section) exposed to between about −40° C. and about 0° C. is $\pi R^2 - 0.25(\pi R^2) = 0.75(\pi R^2)$, which is three times the area of the tissue effectively treated by the ice-ball.

The current strategy used for avoiding excessive damage to adjacent tissues is to use such a single probe of a smaller diameter producing an ice-ball of smaller size, thereby exposing the patient to the danger of malignancy.

Thus, the prior art methods and devices fail to provide effective resolution of treatment along the planes perpendicular to the axis of penetration of the cryosurgical probe into the patient's organ.

Furthermore, since anatomical organs such as the prostate usually feature an asymmetric three dimensional shape, the introduction of a cryosurgical probe along a specific path of penetration within the organ may provide effective treatment to specific regions located at specific depths of penetration but at the same time may severely damage other portions of the organ located at other depths of penetration.

There is thus a widely recognized need for, and it would be highly advantageous to have, cryosurgical method and device which provide high resolution of treatment along the axis of penetration of the cryosurgical probe into the patient's organ as well as along the planes perpendicular to the axis of penetration.

Specifically, there is a widely recognized need for, and it would be highly advantageous to have, high resolution cryosurgical method and device which enable to effectively destroy selective portions of a patient's tissue while minimizing damage to adjacent tissues and organs.

Furthermore, there is a widely recognized need for such method and device which enable to selectively treat various portions of the tissue located at different depths of the organ, thereby effectively freezing selected portions of the tissue while avoiding the damaging of other tissues and organs located at other depth along the axis of penetration.

It would be further advantageous to have such cryosurgical method and device which three dimensionally map an organ of a patient so as to form a three dimensional grid thereof, and which apply a multi-probe system introduced into the organ according to the grid so as to enable systematic high-resolution three dimensional cryosurgical treatment of the organ and selectively destroy the treated tissue with minimal damage to surrounding, healthy, tissues.

SUMMARY OF THE INVENTION

According to the present invention there is provided a high resolution cryosurgical method for treating a patient's prostate, comprising the steps of (a) introducing a plurality of cryosurgical probes to the prostate, the probes having a substantially small diameter, the probes being distributed across the prostate so as to form at least an outer arrangement of probes adjacent to the periphery of the prostate and an inner arrangement of probes adjacent to the prostatic urethra; (b) producing an ice-ball at the end of each of the cryosurgical probes so as to locally freeze a tissue segment of the prostate.

Some or all of the probes may be distributed along the inner and outer arrangements so as to form pairs of probes, each pair including an inner probe adjacent to the prostatic urethra and an outer probe adjacent to the periphery of the prostate. However, since the periphery of the prostate is larger than its core, the number of probes in the outer arrangement typically exceeds the number of probes in the inner arrangement.

Preferably, the diameter of the cryosurgical probes is between about 0.2 and 1.4 millimeters, preferably between about 1 and 1.4 millimeters, typically about 1.2 millimeters, generating ice-balls of about 2 centimeters in diameter or less. As used herein the term "about" refers to ±20%.

The above arrangement of probes ensures the formation of at least two adjacent (e.g., close within less than about 1 millimeter, tangent or overlapping) ice-balls in each prostate section, one being closer to the periphery of the prostate and the other being closer to the urethra, each of the ice-balls featuring a diameter of 2 centimeters or less, thereby ensuring higher resolution and less damage inflicted on surrounding tissues.

Further according to the present invention there is provided a high resolution cryosurgical method for treating a patient's prostate, comprising the step of inserting at least two cryosurgical probes of a small diameter into a prostatic tissue segment extending between the prostatic urethra and the periphery of the prostate, the probes being for producing ice-balls of substantially small diameter so as to provide a temperature of at least about −40° C. to a significant portion of the tissue segment while minimizing the thickness of adjacent tissues exposed to temperatures of between about −40° C. and about 0° C.

Further according to the present invention there is provided a high resolution cryosurgical method for treating a patient's organ, comprising the steps of (a) providing a guiding element including a net of apertures, each aperture being for insertion of a cryosurgical probe therethrough into the patient's organ; (b) providing a set of images of the organ by using an imaging device, such as ultrasound, MRI or CT, the images provide information on specific planes located at specific depths within the organ, each of the images includes a net of marks correlated to the net of apertures of the guiding element, wherein the marks represent the locations of ice-balls, preferably the location of their centers, which may be formed by the cryosurgical probes when introduced through the apertures of the guiding element to the distinct depths within the organ; and (c) introducing the cryosurgical probes to selected depths within the organ according to the information provided by the images and generating the ice-balls.

Further according to the present invention there is provided a high resolution cryosurgical apparatus for treating a patient's organ, comprising (a) a plurality of cryosurgical probes of small diameter, the probes being for insertion into the patient's organ, the probes further being for producing ice-balls for locally freezing selected portions of the organ; (b) a guiding element including a net of apertures for inserting the cryosurgical probes therethrough; (c) an imaging device for providing a set of images, the images being for providing information on specific planes located at specific depths within the organ, each of the images includes a net of marks correlated to the net of apertures of the guiding element, wherein the marks represent the locations of ice-balls, preferably the location of their centers, which may be formed by the cryosurgical probes when introduced through the apertures of the guiding element to the distinct depths within the organ.

Preferably, each of the cryosurgical probes includes a Joule-Thomson cooler.

Further according to the present invention there is provided a high resolution cryosurgical apparatus for treating a patient's organ, comprising (a) a plurality of cryosurgical probes of small diameter for insertion into the organ, each of the probes including a Joule-Thomson cooler, the cryosurgical probes being connectable to a manifold; (b) a manifold for distributing a high pressure gas to the cryosurgical probes, the manifold being in fluid communication with the probes and with a high pressure gas source.

Preferably, the manifold includes a cooling element for pre-cooling the high pressure gas flowing to the cryosurgical probes. The pre-cooling element may include a Joule-Thomson cooler or a cryogenic fluid. Alternatively, the pre-cooling element may include an electrical cooling element or the like.

The present invention successfully addresses the shortcomings of the presently known configurations by providing cryosurgical method and device which provide high resolution of treatment along the axis of penetration of the cryosurgical probe into the patient's organ as well along the planes perpendicular to the axis of penetration.

Furthermore, the present invention successfully addresses the shortcomings of the presently known configurations by providing cryosurgical method and device which enable to effectively destroy selective portions of a patient's tissue while minimizing damage to adjacent tissues and organs.

In addition, the present invention successfully addresses the shortcomings of the presently known configurations by providing cryosurgical method and device which enable to selectively treat various portions of the tissue located at different depths of the organ, thereby effectively destroying selected portions of the tissue while avoiding the damaging of other tissues and organs located along the axis of penetration.

Furthermore, the present invention successfully addresses the shortcomings of the presently known configurations by providing cryosurgical method and device which three dimensionally map an organ of a patient so as to form a three dimensional grid thereof, and which apply a multi-probe system introduced into the organ according to the grid so as to enable high-resolution cryosurgical treatment of the organ.

The gist of the present invention is the three dimensionally controlled high resolution tissue freezing.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1A:
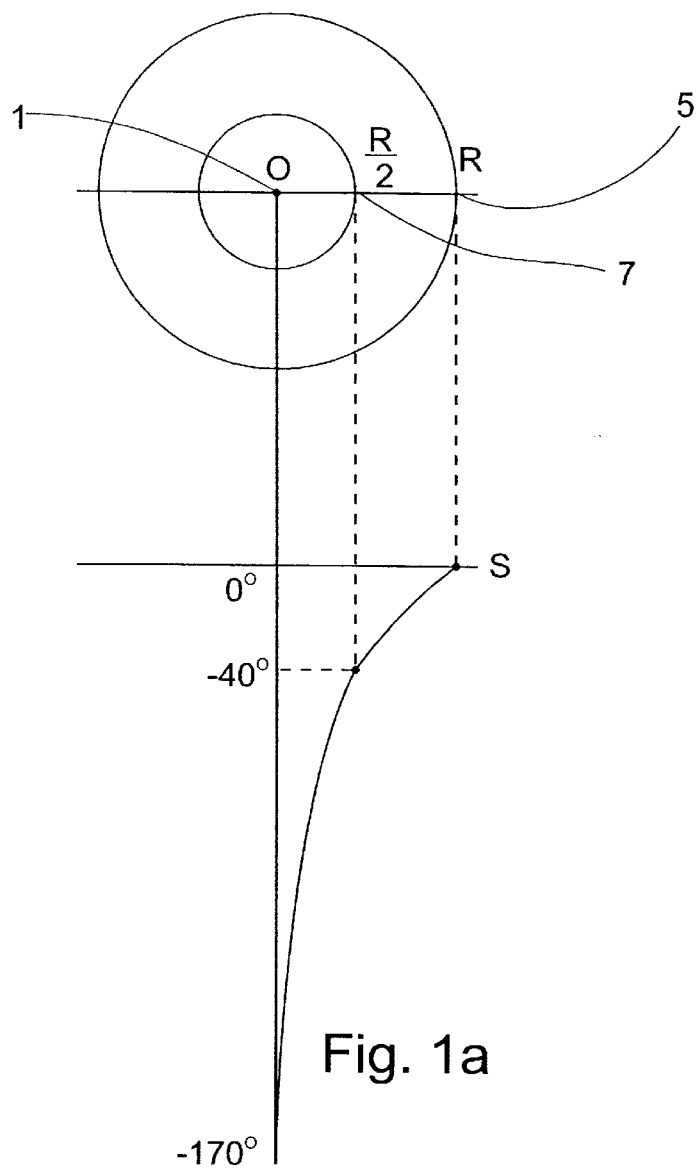
FIG. 1a is a graph showing the profile of temperature distribution within an ice-ball formed at the tip of a cryosurgical probe.

The present invention is of high resolution cryosurgery method and apparatus which enable to effectively and accurately destroy a predetermined portion of a tissue while minimizing damage to adjacent healthy tissues and organs.

The principles and operation of method and apparatus according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIG. 1a illustrates the profile of temperature distribution across an ice-ball formed at the tip of a cryosurgical probe. As shown, the temperature at a surface 5 of the ice-ball is 0° C. The temperature declines exponentially towards a center 1 of the ball where it preferably reaches the value of –170° C., such that an isothermal surface 7 of about –40° C. is typically located within the ice-ball at the half way between the center of the ball and its surface. Thus, if the ice-ball features a radius R, then the radius of the –40° C. isothermal surface 7 is about R/2.

Figure 1B:
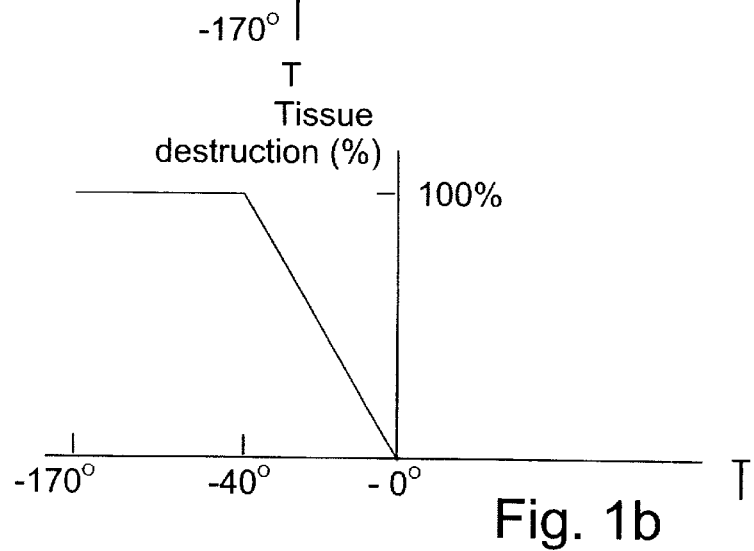
FIG. 1b is a graph showing the effectiveness of a cryosurgical treatment, given in percentage of tissue destruction, as a function of temperature.

FIG. 1b is a graph showing the effectiveness of a cryosurgical treatment (given in percentage of tissue destruction) as a function of temperature. As shown, the temperature required for effectively destroying a tissue is at least about –40° C. Accordingly, in order to effectively destroy a tissue, the isothermal surface of –40° C. (shown in FIG. 1a) should be placed at the periphery of the treated tissue so that the entire area of the treated tissue is exposed to at least about –40° C., thereby exposing adjacent healthy tissues and organs to the external portion of the ice-ball. The application of temperatures of between about –40° C. and 0° C. to such healthy tissues usually causes substantial damage thereto, which damage may result in temporary or permanent impairment of functional organs.

Figure 2A:
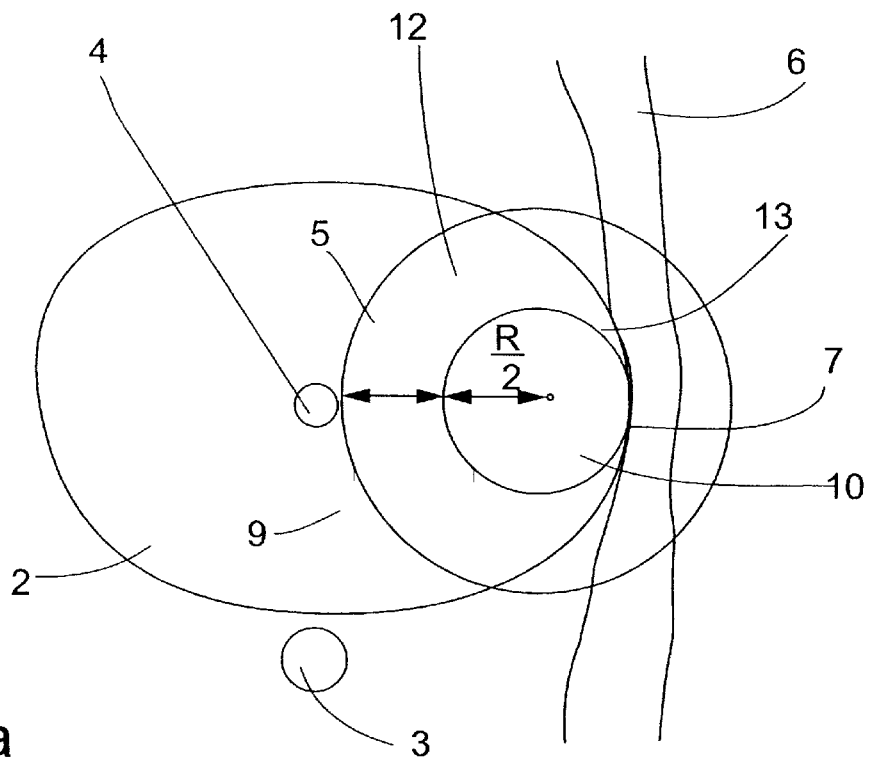
FIGS. 2a–2c are cross sectional views of an ice-ball formed at the tip of a conventional cryosurgical probe introduced into a patient's prostate.
Figure 2B:
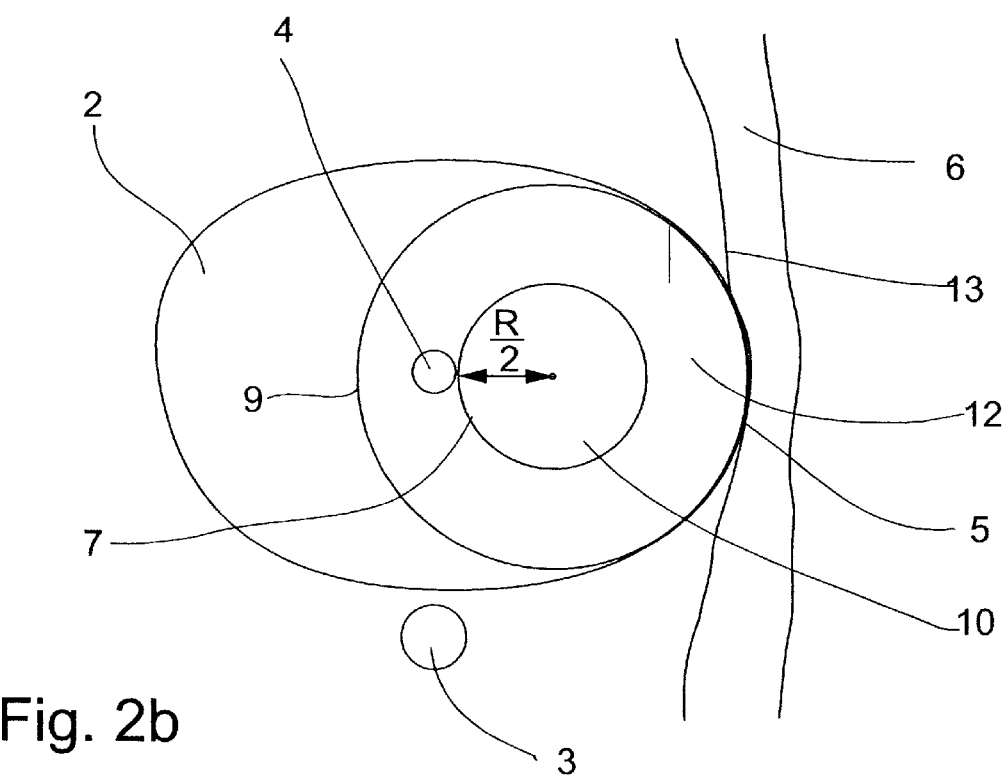
Figure 2C:
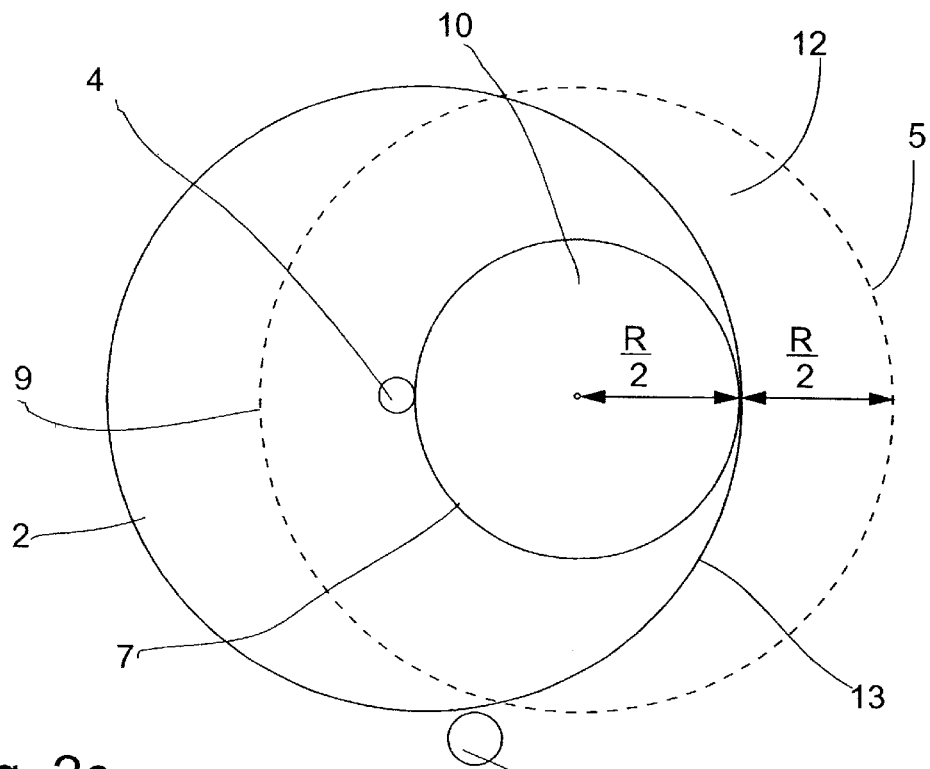

FIGS. 2a–2c illustrate prior-art cryosurgical methods wherein a single cryosurgical probe of a substantially large diameter, typically 3–5 millimeters, is introduced between the patient's prostatic urethra and the periphery of the prostate, so as to destroy the prostatic tissue extending therebetween.

Specifically, FIGS. 2a–2c are cross sectional views of an ice-ball 9 formed at the end of a conventional cryosurgical tip introduced into a prostate 2 of a patient. The patient's prostatic urethra, rectum and nerves are designated as 4, 3, and 6 respectively.

A single ice-ball 9 is formed within the prostatic tissue segment extending between the prostatic urethra 4 and the periphery of the prostate 13. The dimensions of a conventional cryosurgical probe are designed so as to provide an ice-ball 9 having an inner portion 10 extending through a substantially significant portion of such a tissue segment, so as to apply temperatures of between about –170° C. and about –40° C. thereto. The application of a single probe for producing a single ice-ball 9 imposes a trade-off between several options.

FIGS. 2a and 2b illustrate the trade-off between a first option of avoiding the damaging of the patient's prostatic urethra 4 yet damaging nerves 6 present close to the periphery 13 of the prostate 2 (FIG. 2a), and a second option of avoiding the damaging of the patient's nerves 6 yet damaging urethra 4 (FIG. 2b).

As shown in FIG. 2a, the isothermal surface 7 of –40° C. is positioned substantially at the periphery 13 of the patient's prostate 2, such that surface 5 of the ice-ball 9 is positioned substantially near the patient's urethra 4, so as to avoid damaging of the patient's urethra 4. Thus, the inner portion 10 of ice-ball 9 effectively freezes the peripheral regions (in cross section) of the prostate, while outer portion 12 of ice-ball 9 extends through the patient's nerves 6. The application of temperatures of between about –40° C. and 0° C. to the patient's nerves 6 may result in temporary or permanent impairment thereof.

Similarly, when ice-ball 9 is positioned between the patient's urethra 4 and rectum 3 in such a manner so as to avoid the damaging of urethra 4, the application of between about –40° C. and 0° C. to the patient's rectum may result in temporary or permanent impairment thereof.

As shown in FIG. 2b, the isothermal surface 7 of –40° C. is positioned substantially near the patient's urethra 4 such that surface 5 of ice-ball 9 is positioned substantially near the patient's nerves 6 and/or rectum 3 (not shown), so as to avoid damaging of the patient's nerves 6 and/or rectum 3. Thus, inner portion 10 of ice-ball 9 effectively freezes the central regions (in cross section) of prostate 2, while outer portion 12 of ice-ball 9 extends through the patient's urethra 4. The application of temperatures of between about –40° C. and 0° C. to the patient's urethra 4 may result in temporary or permanent impairment thereof.

However, none of the alternatives shown in FIGS. 2a and 2b provides an effective treatment (temperature of at least about –40° C.) to the entire prostatic tissue segment extending between urethra 4 and the periphery 13 of the prostate, thereby exposing the patient to the risk of malignancy.

FIG. 2c shows another possible alternative wherein a thicker cryosurgical probe, having a tip diameter of between 4 and 6 millimeters is used for producing a lager ice-ball, of about 4–5 centimeters in diameter, so as to enable effective treatment of the entire prostatic tissue segment extending between the urethra 4 and periphery 13 of prostate 2. As shown, inner portion 10 of the ice-ball 9 extends through the entire tissue segment (in cross section) between urethra 4 and periphery 13 of the prostate, thereby exposing urethra 4 and nerves (not shown), as well as the rectum 3, to outer portion 12 of the ice-ball 9.

The thickness (in cross section) of tissues exposed to outer portion 12 of the ice-ball is about R/2, wherein R is the radius of ice-ball 9. Thus, the volume of adjacent tissues exposed to damage becomes substantially greater than the volume of the treated tissue.

Thus, the conventional cryosurgical probes and methods fail to provide the necessary resolution of treatment required for enabling an accurate and effective destruction of a tissue while preserving other tissues and organs adjacent thereto.

Figure 3A:
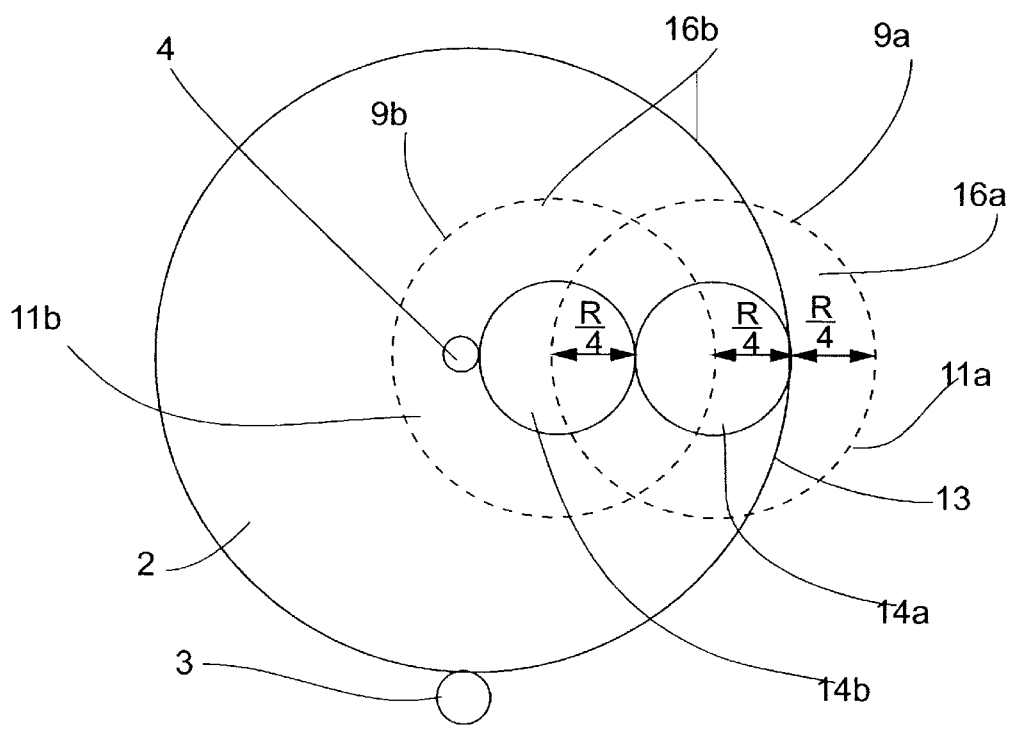
FIGS. 3a–3b are cross sectional views of two ice-balls formed at the tips of cryosurgical probes according to the present invention introduced into a patient's prostate.
Figure 3B:
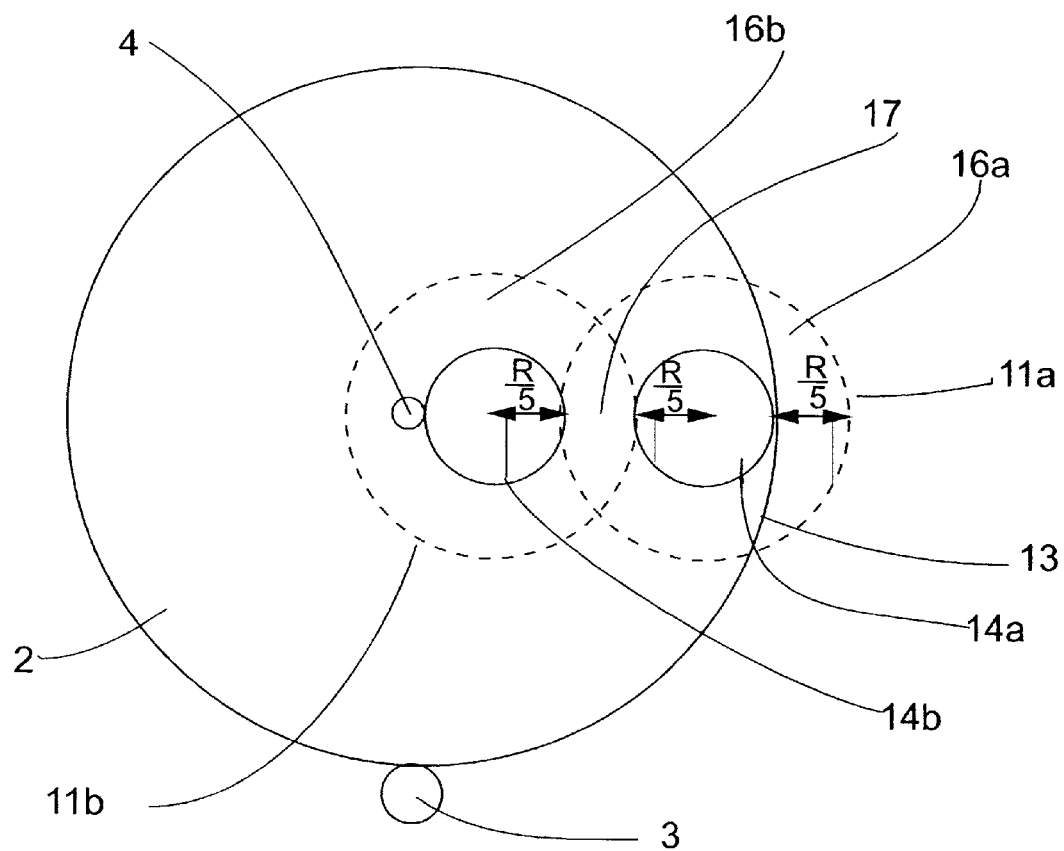

FIGS. 3a and 3b are schematic illustrations of a cryosurgical method according to the present invention, wherein a plurality of cryosurgical probes of substantially small diameters are introduced between the patient's prostatic urethra 4 and periphery 13 of prostate 2, so as to destroy the prostatic tissue extending therebetween.

As shown in FIG. 3a, preferably two probes are introduced into a prostatic tissue segment extending between the patient's prostatic urethra 4 and periphery 13 of prostate 2, so as to form two smaller ice-balls, 9a and 9b.

According to the configuration shown in FIG. 3a, each of ice-balls 9a and 9b features a radius of R/2, which is half the radius of ice-ball 9 shown in FIG. 2c. Accordingly, ice-balls 9a and 9b include respective inner portions, 14a and 14b, each having a radius of R/4, and respective outer portions, 16a and 16b, each having a thickness of R/4.

Therefore, by introducing two probes of a small diameters rather than a single probe of a larger diameter into the tissue segment extending between prostatic urethra 4 and periphery 13 of prostate 2, the thickness of adjacent tissues exposed to damage is substantially decreased. The specific example of FIG. 3a shows that the thickness (in cross section) of adjacent tissues exposed to between about −40° C. and 0° C. is only R/4, which is half the thickness and respectively much less the volume (e.g., 8 fold less), exposed to damage when using the prior art method (shown in FIG. 2c).

By further decreasing the diameter of the cryosurgical probes and introducing a plurality of probes into the tissue segment extending between urethra 4 and periphery 13 of prostate 2, the damage to surrounding tissues may be further minimized, thereby improving the resolution of the cryosurgical treatment.

Another embodiment is shown in FIG. 3b, wherein two probes are introduced into the tissue segment extending between the patient's urethra 4 and periphery 13 of prostate 2, so as to form two ice-balls 9a and 9b, such that inner portion 14a of ice-ball 9a is substantially spaced from inner portion 14b of ice-ball 9b, and outer portion 16a of ice-ball 9a partially overlaps outer portion 16b of ice-ball 9b, the overlapping region being designated as 17. The specific example shown in FIG. 3b is of two ice-balls each having a radius of R/5, wherein R is the radius of a conventional ice-ball as shown in FIG. 2c. By using such configuration, the thickness of adjacent tissues exposed to damage is decreased to R/5 and the volume thereof is decreased respectively. It will be appreciated that in the example given substantial fractions of region 17, from which heat is extracted by two probes, will become cooler than −40° C.

The specific examples shown in FIGS. 3a and 3b are of two ice-balls having tangent and spaced inner portions, respectively. However, a plurality of probes may be used, each having a distinct diameter, the inner portions of which being tangent or spaced.

Figure 4:
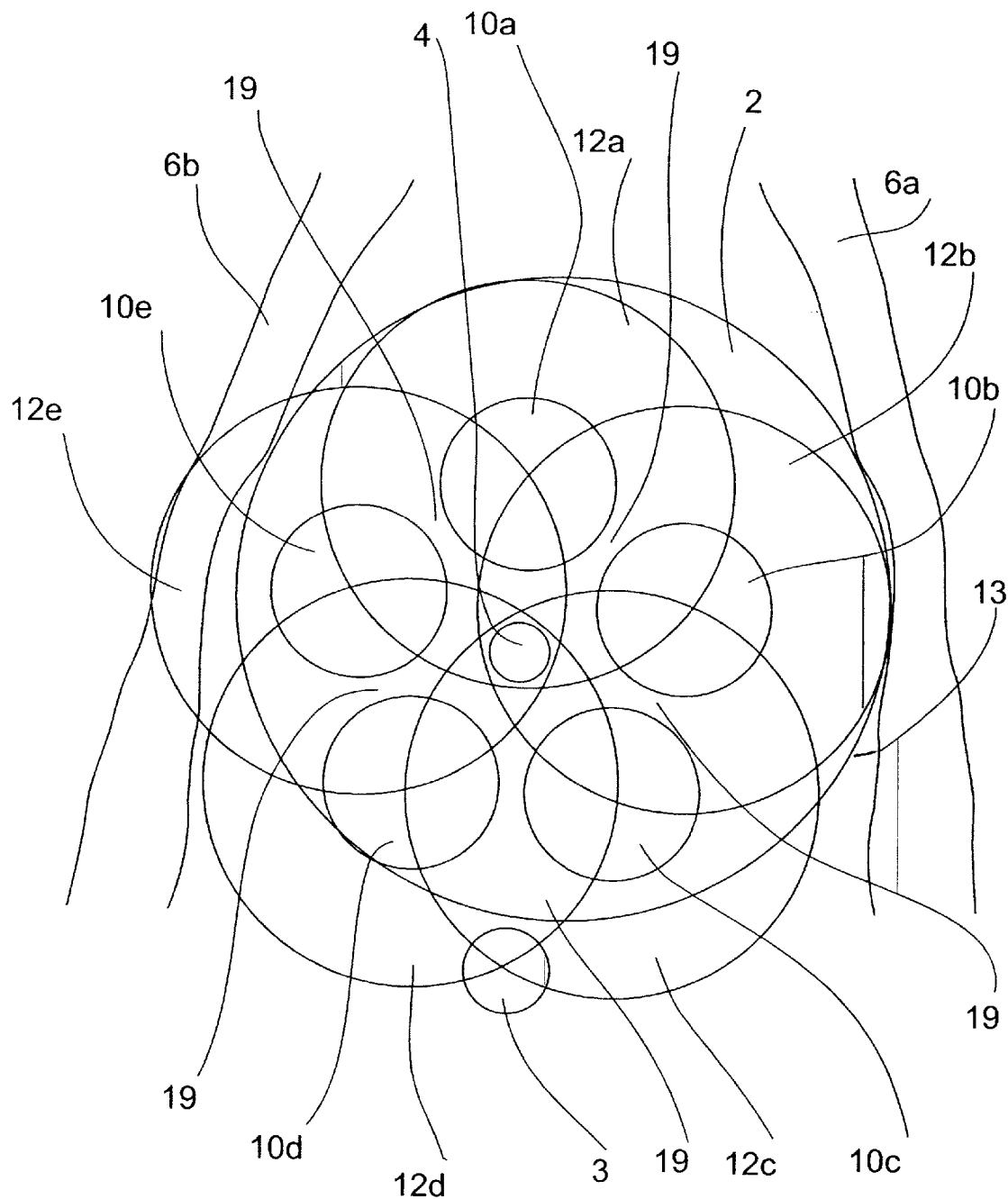
FIG. 4 is a cross sectional view illustrating the conventional method for treating a patient's prostate.

Referring to FIG. 4, a prior-art cryosurgical method is shown, illustrating the distribution of a plurality of cryosurgical probes across a patient's prostate, wherein a single probe is introduce into a tissue segment extending between prostatic urethra 4 and periphery 13 of prostate 2. According to such a prior art method, about 5–7 probes are introduced into the patient's prostate, wherein each of the probes features a diameter of about 3 millimeters. FIG. 4 shows a specific example wherein five probes are introduced so as to form five ice-balls having inner portions 10a–10e and outer portions 12a–12e. As shown, an effective treatment is provided by inner portions 10a–10e, and regions therebetween marked 19, only to limited regions of the prostate, wherein the damage caused to adjacent tissues such as the patient's urethra 4, rectum 3 and nerve 6b by outer portions 12a–12e is considerable.

Figure 5:
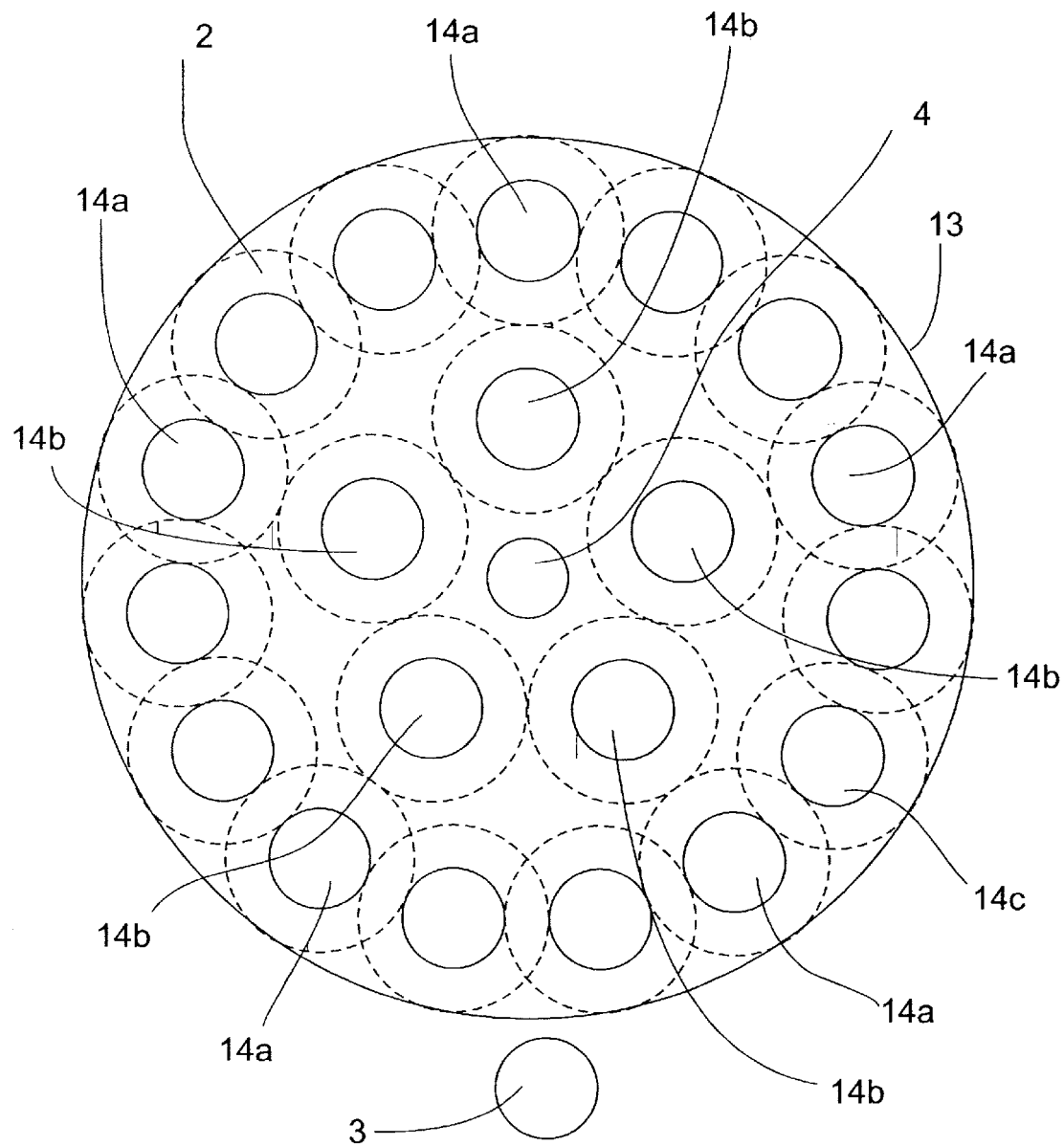
FIG. 5 is a cross sectional view illustrating a method according to the present invention for treating a patient's prostate.

FIG. 5 shows a preferred distribution of cryosurgical probes according to a method of the present invention. As shown, at least two cryosurgical probes of substantially small diameter are introduced into specific segments of prostatic tissue extending between urethra 4 and periphery 13 of prostate 2. FIG. 5 shows a specific example wherein twenty probes are introduced into the patient's prostate 2, including five pairs of inner and outer cryosurgical probes located at specific segments of the prostate extending from the urethra 4 to periphery 13, and additional (five pairs in the example given) of outer cryosurgical probes are introduced therebetween. The inner portions of the ice-balls formed by the pairs of outer and inner probes are designated as 14a and 14b, respectively, wherein the inner portions of the ice-balls formed therebetween are designated as 14c.

The diameter of a single cryosurgical probe according to the present invention is preferably between about 1.2 millimeters and about 1.4 millimeters.

As shown, such distribution of substantially small diameter cryosurgical probes enables to provide an effective treatment of at least −40° C. to a larger area of the prostatic tissue while substantially minimizing the thickness of healthy adjacent tissues exposed to damage.

Thus, a method according to the present invention substantially increases the effectiveness and resolution of treatment relative to the prior art method.

The pattern of distribution of probes shown in FIG. 5 includes an inner circle and an outer circle of probes, wherein a portion of the probes is arranged in pairs of an inner probe and an outer probe. According to another configuration (not shown), the probes are arranged in an inner circle and an outer circle, but not necessarily in pairs of an inner probe and an outer probe.

The probes may be sequentially introduced to and extracted from the patient's prostate so as to sequentially freeze selected portions thereof. A method of quick extraction of the probes without tearing pieces of tissue from the patient, which stick to the tip of the probe, is disclosed hereinunder.

The introduction of a plurality of small diameter cryosurgical probes improves the resolution of treatment along the planes perpendicular to the axis of penetration of the probes into the prostate. However, the prostate, as other anatomical organs, features an asymmetric three dimensional shape. Thus, a specific pattern of distribution of probes may provide an effective treatment to a distinct plane located at a specific depth of penetration, but at the same time may severely damage non-prostatic tissues located at other depths of penetration. The prior art fails to provide cryosurgical method and apparatus which enable high resolution of treatment along and perpendicular to the axis of penetration of the probes into a patient's organ.

According to the present invention there are provided cryosurgical method and apparatus which enable high resolution of treatment along the axis of penetration of the cryosurgical probe into the patient's organ as well as along the planes perpendicular to the axis of penetration, wherein these high resolutions are achieved by forming a three-dimensional grid of the organ, preferably by using ultrasound imaging, and inserting each of the cryosurgical probes to a specific depth within the organ according to the information provided by the grid.

Figure 6:
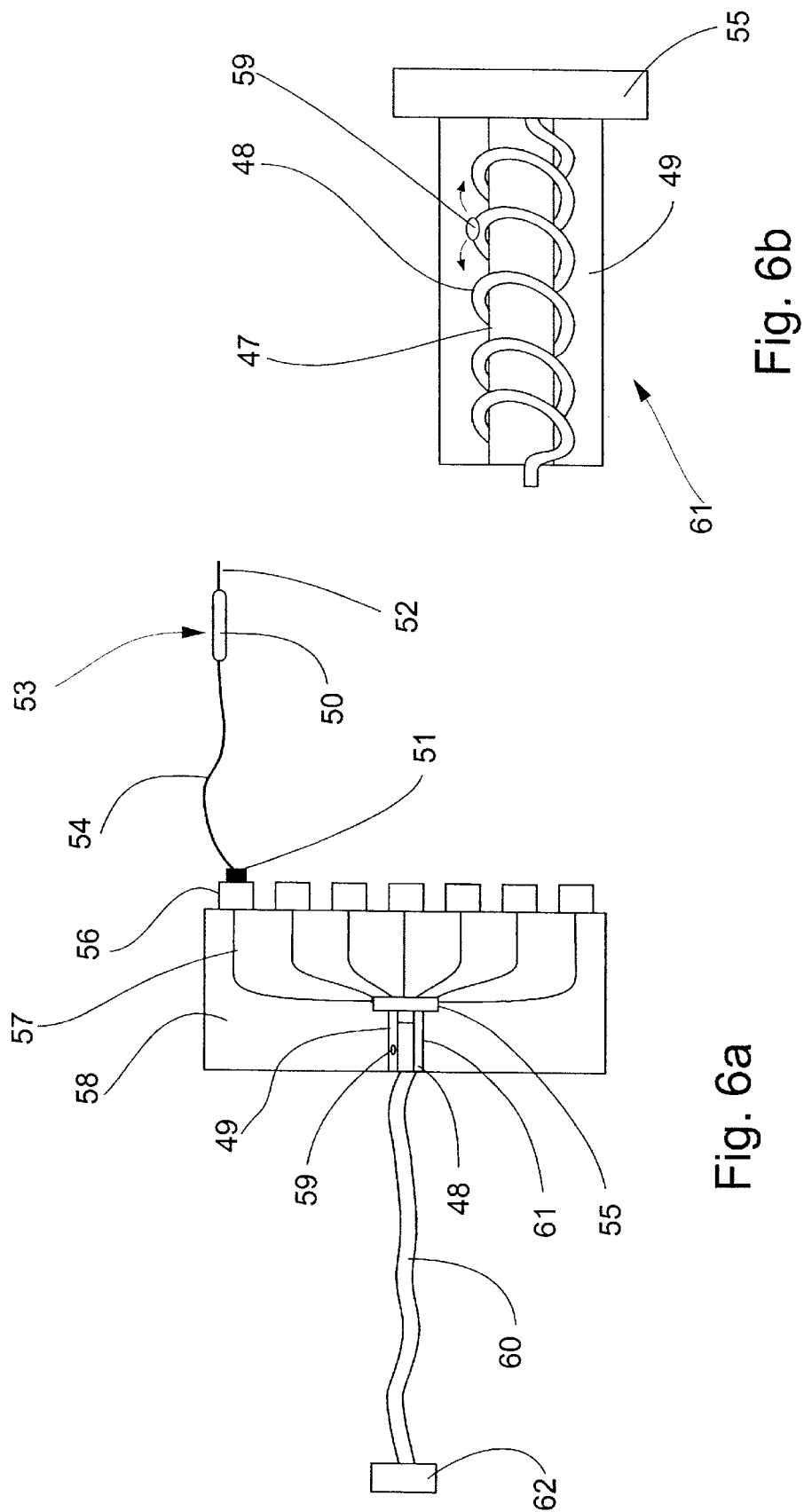
FIG. 6a is a schematic illustration of a multi-probe cryosurgical device according to the present invention.
FIG. 6b is a schematic illustration of a pre-cooling element according to the present invention.
Figure 7:
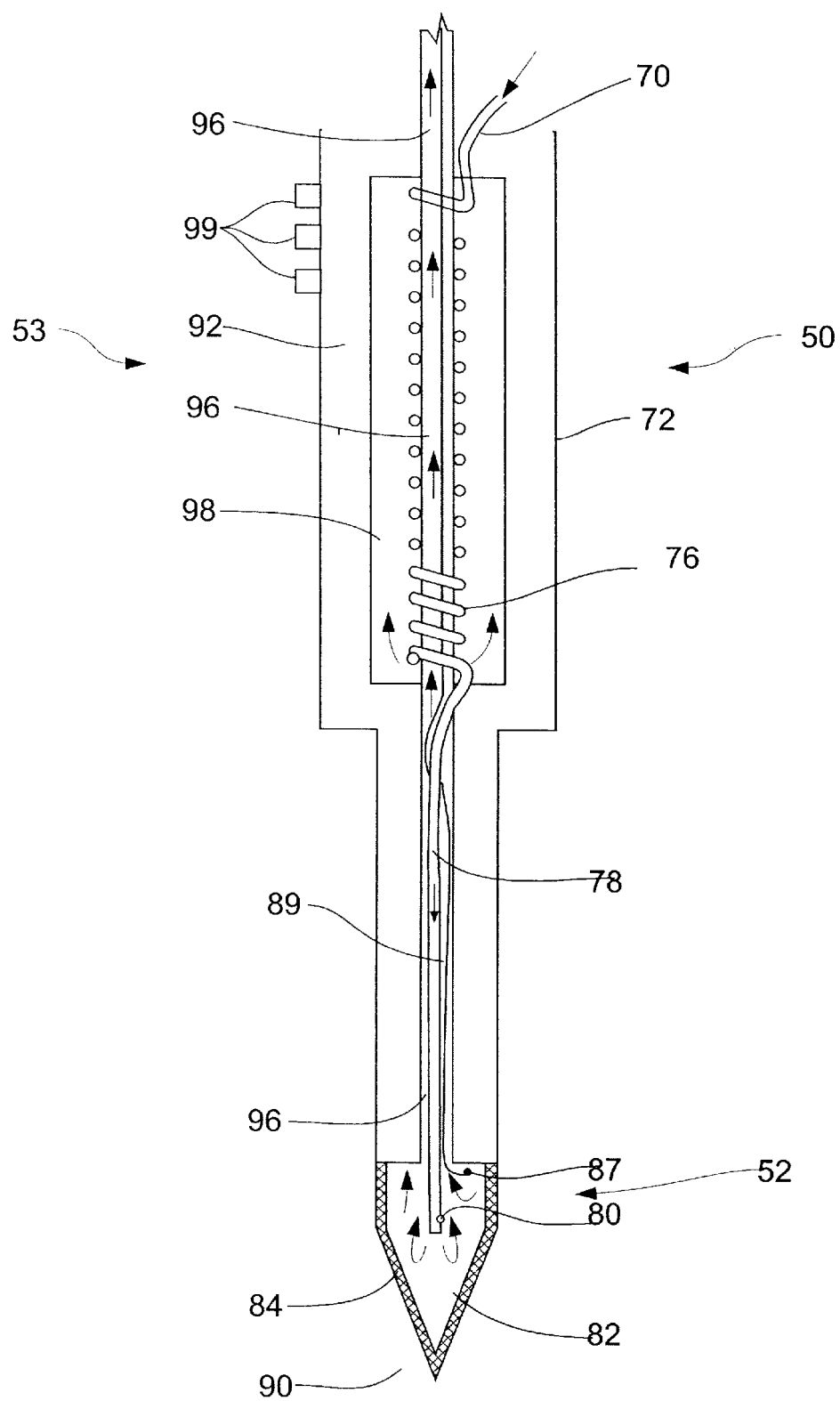
FIG. 7 is a schematic longitudinal section of a preferred cryosurgical probe according to the present invention.

Referring to FIGS. 6a, 6b and 7, a cryosurgical apparatus according to the present invention includes a plurality of cryosurgical probes 53, each having an operating tip 52 including a Joule-Thomson cooler for freezing a patient's tissue and a holding member 50 for holding by a surgeon. As shown in FIG. 7, operating tip 52 includes at least one passageway 78 extending therethrough for providing gas of high pressure to orifice 80 located at the end of operating tip 52, orifice 80 being for passage of high pressure gas therethrough, so as to cool operating tip 52 and produce an ice-ball at its end 90. Gases which may be used for cooling include, but are not limited to argon, nitrogen, air, krypton, $CO_2$, $CF_4$, xenon, or $N_2O$.

When a high pressure gas such as argon expands through orifice 80 it liquefies, so as to form a cryogenic pool within chamber 82 of operating tip 52, which cryogenic pool effectively cools surface 84 of operating tip 52. Surface 84 of operating tip 52 is preferably made of a heat conducting material such as metal so as to enable the formation of an ice-ball at end 90 thereof.

Alternatively, a high pressure gas such as helium may be used for heating operating tip 52 via a reverse Joule-Thomson process, so as to enable treatment by cycles of cooling-heating, and further for preventing sticking of the probe to the tissue when extracted from the patient's body, and to enable fast extraction when so desired.

When a high pressure gas such as helium expands through orifice 80 it heats chamber 82, thereby heating surface 84 of operating tip 52.

Operating tip 52 includes at least one evacuating passageway 96 extending therethrough for evacuating gas from operating tip 52 to the atmosphere.

As shown FIG. 7, holding member 72 may include a heat exchanger for pre-cooling the gas flowing through passageway 78. Specifically, the upper portion of passageway 78 may be in the form of a spiral tube 76 wrapped around evacuating passageway 96, the spiral tube being accommodated within a chamber 98. Thus, gas evacuated through passageway 96 may pre-cool the incoming gas flowing through spiral tube 76.

As further shown in FIG. 7, holding member 72 may include an insulating body 92 for thermally insulating the heat exchanger from the external environment.

Furthermore, operating tip 52 may include at least one thermal sensor 87 for sensing the temperature within chamber 82, the wire 89 of which extending through evacuating passageway 96 or a dedicated passageway (not shown).

In addition, holding member 72 may include a plurality of switches 99 for manually controlling the operation of probe 53 by a surgeon. Such switches may provide functions such as on/off, heating, cooling, and predetermined cycles of heating and cooling by selectively and controllably communicating incoming passageway 70 with an appropriate external gas container including a cooling or a heating gas.

As shown in FIG. 6a, each of cryosurgical probes 53 is connected via a flexible connecting line 54 to a connecting site 56 on a housing element 58, preferably by means of a linking element 51. Cryosurgical probes 53 may be detachably connected to connecting sites 56.

Preferably, evacuating passageway 96 extends through connecting line 54, such that the outgoing gas is evacuated through an opening located at linking element 51 or at any other suitable location, e.g., manifold 55, see below. Preferably, line 54 further includes electrical wires for providing electrical signals to the thermal sensor and switches (not shown).

Each of cryosurgical probes 53 is in fluid communication with a manifold 55 received within a housing 58, manifold 55 being for distributing the incoming high pressure gas via lines 57 to cryosurgical probes 53.

As shown, housing 58 is connected to a connector 62 via a flexible cable 60 including a gas tube (not shown), connector 62 being for connecting the apparatus to a high pressure gas source and an electrical source.

The apparatus further includes electrical wires (not shown) extending through cable 60 and housing 58 for providing electrical communication between the electrical source and cryosurgical probes 53.

Preferably, housing 58 includes a pre-cooling element, generally designated as 61, for pre-cooling the high pressure gas flowing to cryosurgical probes 53. Preferably, pre-cooling element 61 is a Joule-Thomson cooler, including a tubular member 48 received within a chamber 49, tubular member 48 including an orifice 59 for passage of high pressure gas therethrough, so as to cool chamber 49, thereby cooling the gas flowing through tubular member 48 into manifold 55.

Another configuration of a pre-cooling element 61 is shown in FIG. 6b, wherein tubular member 48 is in the form of a spiral tube wrapped around a cylindrical element 47, so as to increase the area of contact between tubular member 48 and the cooling gas in chamber 49.

According to yet another configuration (not shown), housing 58 includes a first tubular member for supplying a first high pressure gas to manifold 55, and a second tubular member for supplying a second high pressure gas to pre-cooling element 61. Any combination of gases may be used for cooling and/or heating the gases flowing through such tubular members.

Alternatively, a cryogenic fluid such as liquid nitrogen may be used for pre-cooling the gas flowing through housing 58. Alternatively, an electrical pre-cooling element may used for pre-cooling the gas.

Preferably, thermal sensors (not shown) may be located within cable 60 and manifold 55 for measuring the temperature of gas flowing therethrough.

Figure 8:
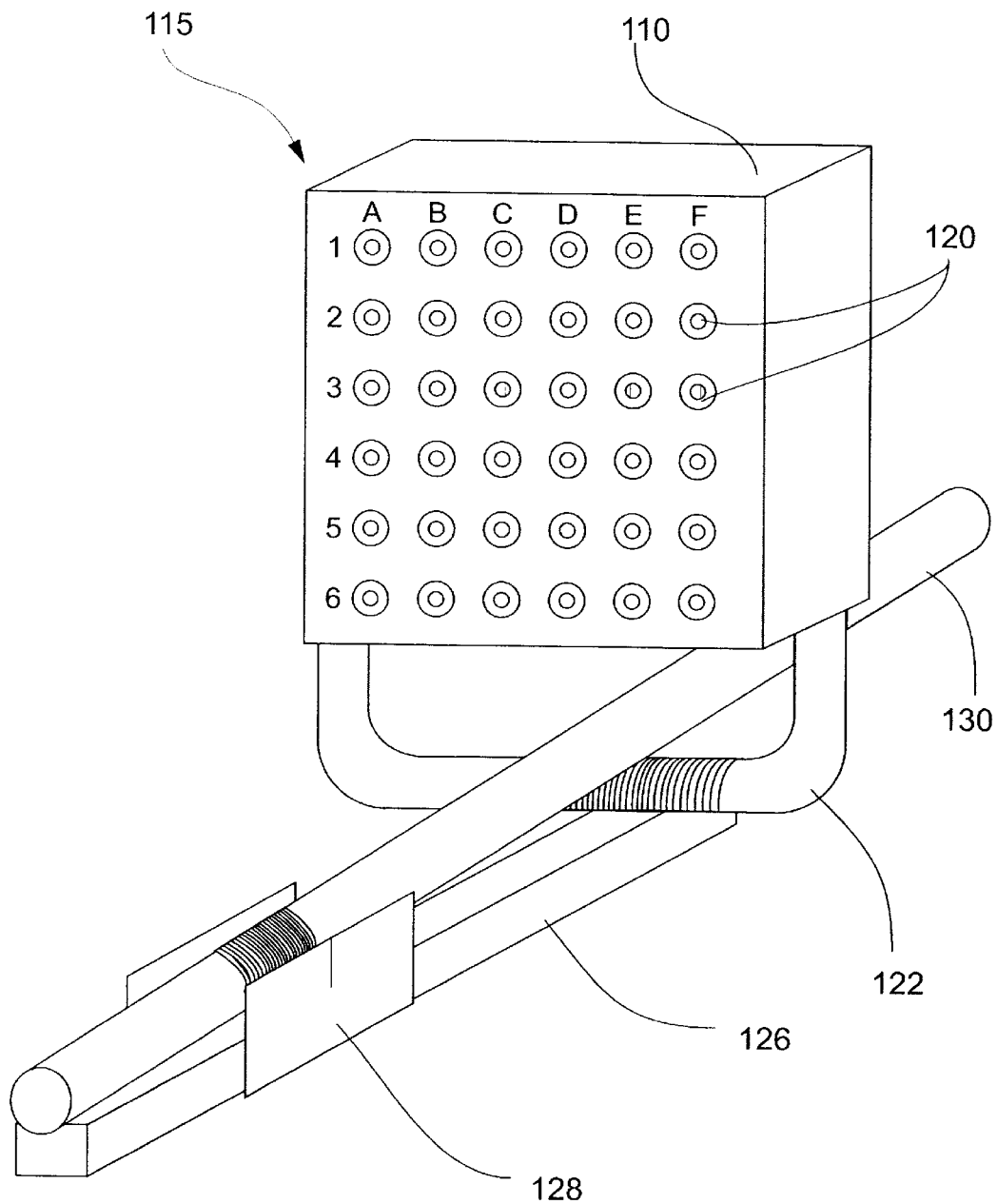
FIG. 8 is a perspective view of a guiding element for receiving cryosurgical probes according to the present invention, the guiding element being connected to an ultrasound probe.
Figure 9:
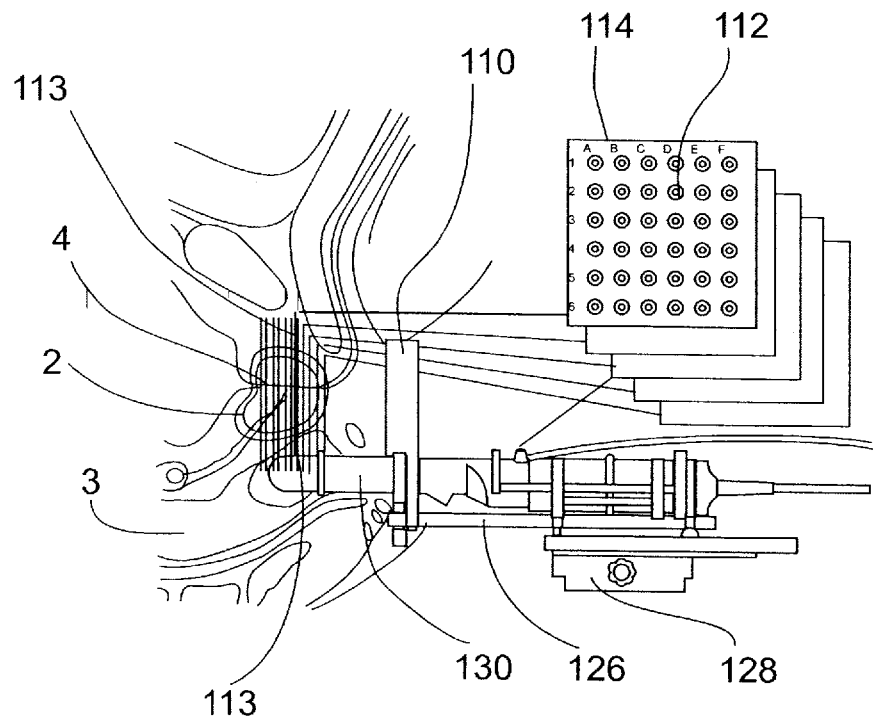
FIGS. 9 and 10 illustrate a method according to the present invention including the steps of forming a three-dimensional grid of a patient's prostate and introducing cryosurgical probes thereto.
Figure 10:
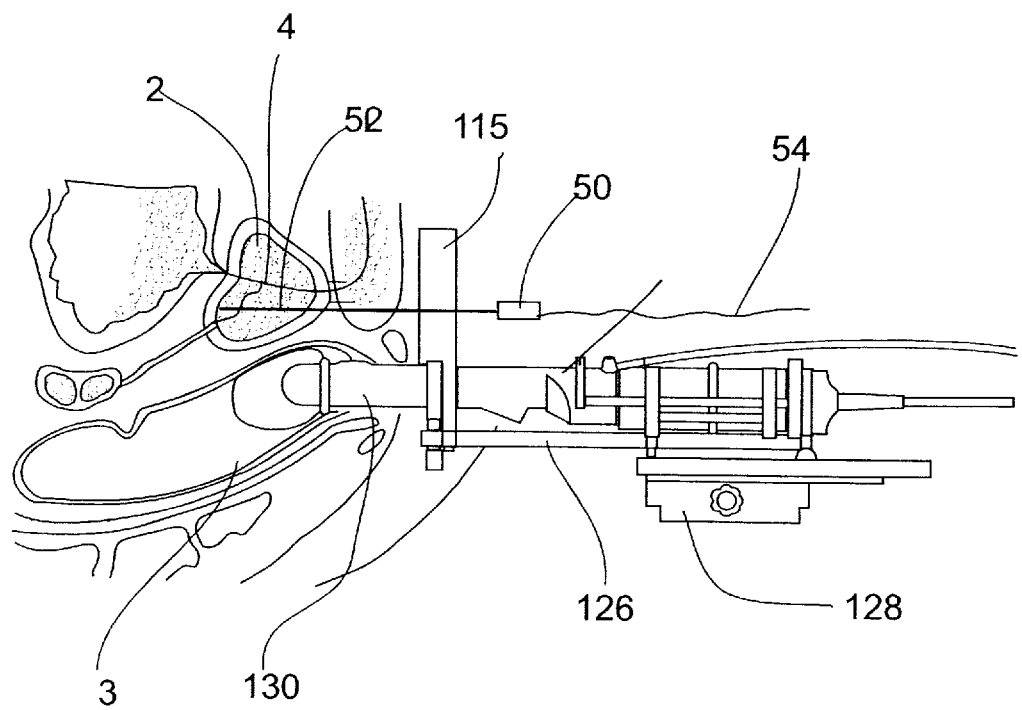

Referring to FIGS. 8–10, method and apparatus according to the present invention applies an imaging device such as ultrasound, MRI or CT, so as to form a three-dimensional grid of the patient's treated organ, e.g., prostate, the three dimensional grid serves for providing information on the three dimensional shape of the organ. Each of the cryosurgical probes is then inserted to a specific depth within the organ according to the information provided by the grid.

As shown in FIG. 8, an ultrasound probe 130 is provided for insertion into the patient's rectum, ultrasound probe 130 being received within a housing element 128. A guiding element 115 is connected to housing element 128 by means of a connecting arm 126. As shown, guiding element 115 is in the form of a plate 110 having a net of apertures 120, each aperture serves for insertion of a cryosurgical probe therethrough. Preferably, the distance between each pair of adjacent apertures 120 is between about 2 millimeters and about 5 millimeters.

As shown in FIG. 9, ultrasound probe 130 is introduced to a specific depth 113 within the patient's rectum 3. A net of marks 112 is provided on the obtained ultrasound image 114, the net of marks 112 on image 114 being accurately correlated to the net of apertures 120 on guiding element 115.

Thus, marks 112 on image 114 sign the exact locations of the centers of ice-balls which may be formed at the end of the cryosurgical probes inserted through apertures 120 to the patient's prostate 2, wherein image 114 relates to a specific depth of penetration 113 of the cryosurgical probes into the prostate 2.

As shown in FIG. 9, ultrasound probe 130 is gradually introduced to various depths 113 of rectum 3, thereby producing a set of images 114, wherein each image relates to a respective depth of penetration into the prostate 2. Thus, each of images 114 relates to a specific plane perpendicular to the axis of penetration of the cryosurgical probes.

The set of images 114 provides a three dimensional grid of the prostate. Such three-dimensional grid is then used for planning the cryosurgical procedure.

For example, the introduction of a cryosurgical probe along a given axis of penetration to a first depth may effectively destroy a prostatic tissue segment, while introduction of the probe to a second depth may severely damage the prostatic urethra.

Since the ice-ball is locally formed at the end of the cryosurgical probe, each probe may be introduced to a specific depth so as to locally provide an effective treatment to a limited portion of the prostate while avoiding the damaging of non-prostatic or prostatic tissues located at other depths of penetration.

FIG. 10 shows the insertion of an operating tip 52 of a cryosurgical probe 50 through an aperture of guiding element 115 into the prostate 2 of a patient.

Preferably, a plurality of cryosurgical probes are sequentially inserted through apertures 120 of guiding element 115 into the patient's prostate, wherein each probe is introduced to a specific depth, thereby providing substantially local effective treatment to distinct segments of the prostatic tissue while avoiding the damaging of other prostatic or nonprostatic tissue segments.

Preferably, each of the cryosurgical probes includes a scale for indicating the depth of penetration into the prostate.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A high resolution cryosurgical method for treating an organ of a patient, the method comprising the steps of:

(a) providing a three dimensional imaging device and three-dimensionally imaging at least a portion of the organ so as to provide a three dimensional grid of at least said portion of the organ and to determine boundaries of a tissue segment of the organ for treatment;

(b) providing a guiding element including an array of guiding apertures, each of said guiding apertures being adapted for insertion and guidance of a cryosurgical probe there through, and based on information extractable from said three dimensional grid of at lest said portion of the organ positioning said guiding element with respect to the patient;

(c) introducing through selected guiding apertures of said guiding element a plurality of cryosurgical probes into the organ, each of said cryosurgical probes being inserted to a desired depth and having a substantially small diameter, said probes being distributed across and along the organ, so as to form a three dimensional arrangement of probe heads in the organ, said arrangement of probe heads is selected such that by producing an ice-ball at a head of said probe heads said tissue segment of the organ locally freezes while minimizing damage to surrounding tissues; and (d) producing said ice-ball at said head of each of said cryosurgical probes, so as to locally freeze said tissue segment of the organ, while minimizing damage to said surrounding tissues.

2. The method of claim 1, wherein said organ is a prostate.

3. The method of claim 1, wherein said diameter of said cryosurgical probes is between about 0.2 millimeters and about 1.4 millimeters.

4. The method of claim 1, wherein said cryosurgical probes are sequentially introduced to and extracted from the organ via said guiding apertures so as to sequentially freeze specific portions of the organ.

5. The method of claim 1, wherein said cryosurgical probes are also actively heatable.

6. The method of claim 1, wherein the temperature at the center of said ice-balls is between about −40 and about −170° C.

7. The method of claim 1, wherein said step of three-dimensionally imaging at least said portion of the organ is effected by an ultrasound probe for obtaining ultrasound images of a plurality of planes of the organ.

8. The method of claim 1, wherein said ultrasound probe is guided via a housing element.

9. The method of claim 1, wherein said step of positioning said guiding element with respect to the patient is effected via an element physically connecting said guiding element and said three dimensional imaging device, so as to form a positional relationship between said array of guiding apertures and said three dimensional grid of at least said portion of the organ.

10. The method of claim 1, wherein said step of three-dimensionally imaging at least said portion of the organ is effected by magnetic resonance imaging.

11. The method of claim 1, wherein each of said plurality of cryosurgical probes is connected to a source of cryogenic agent through a manifold common to all of said plurality of cryosurgical probes.

12. The method of claim 11, wherein said manifold is precooled during said treatment.

13. The method of claim 1, wherein each of said plurality of cryosurgical probes is selected from the group consisting of a Joule-Thomson probe and a cryogenic fluid probe.

* * * * *